United States Patent [19]

O'Connor et al.

[11] Patent Number: 5,545,151

[45] Date of Patent: Aug. 13, 1996

[54] CATHETER HAVING HYDROPHOBIC PROPERTIES

[75] Inventors: Michael G. O'Connor, Blaine; Eric M. Lovgren, Buffalo, both of Minn.

[73] Assignee: Schneider (USA) Inc, Plymouth, Minn.

[21] Appl. No.: 343,153

[22] Filed: Nov. 22, 1994

[51] Int. Cl.$^6$ .................................................. A61M 25/00
[52] U.S. Cl. .......................... 604/282; 604/264; 138/138
[58] Field of Search ................................. 604/282, 281, 604/280, 264, 265, 51; 128/656–658; 138/134, 138, 123–125, 137–139, 74 139, 140, 141, 143–145

[56] References Cited

U.S. PATENT DOCUMENTS

| | | | |
|---|---|---|---|
| 4,863,442 | 9/1989 | De Mello | 604/282 |
| 4,898,591 | 2/1990 | Jang et al. | 604/282 |
| 4,998,923 | 3/1991 | Samson et al. | 606/194 |
| 5,045,072 | 9/1991 | Castillo et al. | 604/658 |
| 5,078,702 | 1/1992 | Pomeranz | 604/282 |
| 5,085,649 | 2/1992 | Flynn | 604/264 |
| 5,221,270 | 6/1993 | Parker | 604/282 |
| 5,256,144 | 10/1993 | Kraus et al. | 604/96 |
| 5,279,596 | 1/1994 | Castaneda et al. | 604/282 |
| 5,318,032 | 6/1994 | Lonsbury et al. | 604/282 |
| 5,403,292 | 4/1995 | Ju | 604/282 |
| 5,458,935 | 10/1995 | Alzner | 604/280 |
| 5,472,435 | 12/1995 | Sutton | 604/280 |

OTHER PUBLICATIONS

Estane Literature, "Estane Thermoplastic Polyurethane" Product Data, USP XIX VI Class Estane Products.
"Estane Thermoplastic Polyurethane, Product Data, Technical Service Report TSR 73–03/TF–116, Extrusion of Estane Thermoplastic Polyurethanes".

Primary Examiner—Corrine M. McDermott
Assistant Examiner—Ronald K. Stright, Jr.
Attorney, Agent, or Firm—Peter C. Richardson; Lawrence C. Akers; Philip C. Strassburger

[57] ABSTRACT

An intravascular catheter having an elongated tubular body with a proximal portion, a distal portion and a lumen extending therebetween. The tubular body is formed with: (a) an inner layer of a blend of (i) about 10–25 weight percent of a polyester-polyurethane having a durometer of from about 45D–55D, and (ii) about 38–53 weight percent of a polyester polyurethane having a durometer of from about 65D–75D; (b) a reinforcing means at least partially surrounding the inner layer; and (c) an outer layer comprising a blend of (i) about 10–25 weight percent of a polyester-polyurethane having a durometer of from about 45D–55D and (ii) about 38–53 weight percent of a polyester-polyurethane having a durometer of from about 659D–75D.

21 Claims, 4 Drawing Sheets

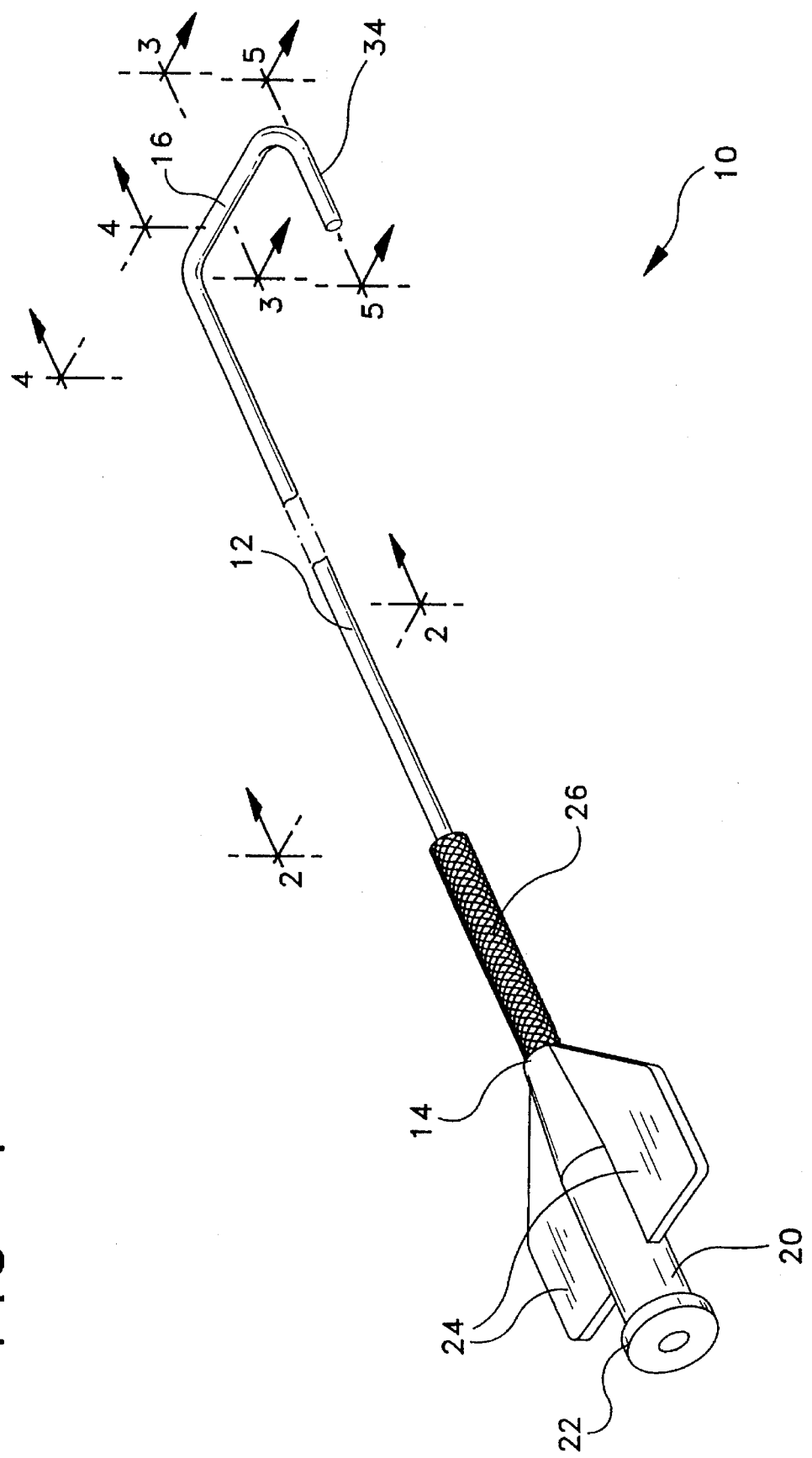

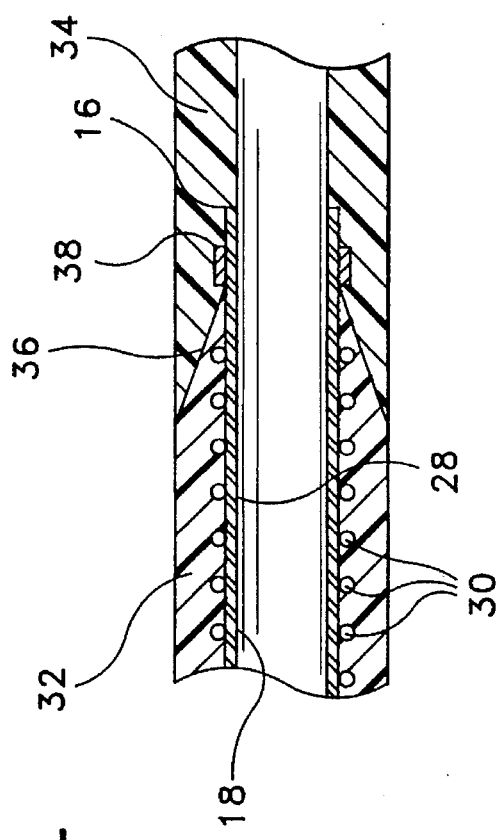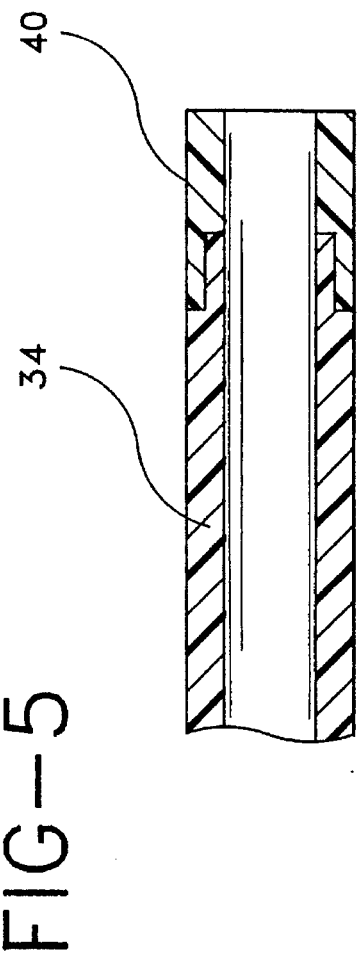

CATHETER HAVING HYDROPHOBIC PROPERTIES

BACKGROUND OF THE INVENTION

The present invention relates to intravascular catheters, and more particularly to a diagnostic catheter having a relatively small outside diameter for its relatively large diameter internal lumen and which possesses good pushability and torqueability properties. The catheter is made of polyester-polyurethane blends.

In evaluating the progress of coronary artery disease in patients, angiography procedures are used to view the patency of selected blood vessels. In carrying out this procedure, a diagnostic catheter having a desired distal end curvature configuration is introduced into the femoral artery using the Seldinger technique and advanced over a guide wire through the vascular system of the patient until the distal end of the catheter is steered into the particular coronary artery to be examined. With smaller patients, a brachial approach may be used.

In that the path taken by the diagnostic catheter is quite tortuous, it is essential to a good diagnostic catheter that it can be steered by torquing its proximal hub and that the torque be transmitted to the distal end in a smooth, controllable fashion. Moreover, the catheter must have sufficient strength in the longitudinal direction so as not to kink or fold as it is advanced through the vascular system. It must also possess a lubricous core lumen to facilitate passage of a guidewire or possibly another catheter therethrough.

It is also a desirable feature of a diagnostic catheter that it possess a relatively large lumen to allow fluids, such as radiopaque contrast fluid to be injected therethrough and out the distal end so that the area of the vascular system under investigation can be viewed fluoroscopically.

It is also a desirable feature of a diagnostic catheter that it have hydrophobic properties. Such hydrophobic properties prevent the device from swelling in a moist environment, so that torqueability is maintained and the catheter will not kink when pushed into position.

The desirable properties of a catheter having a relatively small O.D. and a relatively large I.D. dictates a fairly thin wall. To maintain the desired torqueability and pushability characteristics of a thin wall catheter calls for considerable ingenuity in the formulation of the materials employed and the constructional techniques utilized.

The present invention provides a diagnostic catheter having a desirable O.D. and I.D. while still maintaining the necessary torqueability and pushability characteristics. Using the method and the constituents for the various layers set forth herein, it has been possible to design a diagnostic catheter having, for example, a 4 Fr O.D. but with an internal lumen that is as large as the internal lumen of a 5 Fr catheter that is currently commercially available. Similarly, a 6 Fr catheter made in accordance with the present invention possesses an internal lumen that is about equal to that of a commercially-available 7 Fr catheter.

SUMMARY OF THE INVENTION

In accordance with the present invention there is provided a diagnostic intravascular catheter having an elongated tubular body with a proximal portion, a distal portion and a lumen extending therebetween. The tubular body has an inner layer of a blend of (i) about 10–25 weight percent of a polyester-polyurethane having a durometer of from about 45D–55D, and (ii) about 38–53 weight percent of a polyester polyurethane having a durometer of from about 65D–75D; (b) a reinforcing means at least partially surrounding said inner layer; and (c) an outer layer of a blend of (i) about 10–25 weight percent of a polyester-polyurethane having a durometer of from about 45D–55D, and (ii) about 38–53 weight percent of a polyester-polyurethane having a durometer of from about 65D–75D, said outer layer at least partially covering said reinforcing means. Preferably, the inner layer has a blend of (i) about 10–25 weight percent 50D polyester-polyurethane, and (ii) about 38–53 weight percent 70D polyester polyurethane; and the outer layer has a blend of (i) about 10–25 weight percent 50D polyester-polyurethane, and (ii) about 38–53 weight percent 70D polyester-polyurethane. The intravascular catheter may further include an annular soft-tip member bonded to said distal end of said tubular body member and having a hardness of about 80A. A tubular stem member may be interposed between and bonded to both said tubular body and said soft-tip member, said stem member being a blend of (i) about 10–25 weight percent of a polyester-polyurethane having a durometer of from about 20D–30D, and (ii) about 38–53 weight percent of a polyester-polyurethane having a durometer of from about 65D–75D. Preferably, the stem member will have a blend of (i) about 10–25 weight percent 25D polyester-polyurethane and (ii) about 38–53 weight percent 70D polyester-polyurethane.

In preferred embodiments, the inner layer will have a blend of about 10 weight percent 50D polyester-polyurethane and about 53 weight percent 70D polyester-polyurethane; or a blend of about 15 weight percent 50D polyester-polyurethane and about 48 weight percent 70D polyester-polyurethane; or a blend of about 20 weight percent 50D polyester-polyurethane and about 43 weight percent 70D polyester-polyurethane.

Optionally, the intravascular catheter may have a wall thickness of about 0.0025 inches (0.0064 cm), and said wall thickness may provide an outer diameter to said tubular body in the range of from 3 French to 8 French. The reinforcing means may be totally embedded between said inner layer and outer layer. The outer layer may further comprise a radiopaque filler material. The stem member may include a radiopaque filler material. The tubular body and the tubular stem may have the same outer diameter. The tubular stem member may be tapered from a first outside diameter equal to an outside diameter of said tubular body at a junction between said tubular body and said tubular stem member to a lesser diameter. The lumen may be of a diameter in the range of from about 0.026 to 0.080 inch (0.066 to 0.203 cm) and said outer layer may have an outer diameter in the range of from about 0.039 to 0.110 inch (0.099 to 0.279 cm). The reinforcing means may be a braided metal sleeve configuration of filaments and said sleeve may extend from said proximal portion of the tubular body toward the distal portion of the tubular body by a predetermined distance. The reinforcing means may be a perforated metal tube, a polymer mesh, a polymer tube, or a polymer fabric.

The inner layer is made of polyester-polyurethane blends that are hydrophobic, meaning that they do not absorb moisture and swell. Surrounding this inner layer is a reinforcing means. The reinforcing means may comprise braided filaments and may constrict the inner layer, creating microscopic bumps on the wall surface defining the lumen, effectively decreasing the contact area between an inserted guidewire and the wall surface. The reinforcing means may alternatively consist of a perforated metal tube, a perforated plastic tube, plastic mesh, or plastic fabric.

When attempts are made to thermally bond a soft-tip or a stem member to a braid-reinforced tubular body, the cut free ends of the wires comprising the braid may distort due to heat and penetrate through the heat-softened wall of the tubular body either into the lumen or through the outer wall. To obviate this problem, the catheter of the present invention may incorporate a ring or band formed from a suitable metal or from a high temperature resistant plastic, such as polyimide sold under the trademark, KAPTON. This thin ring captures the ends of the wires comprising the braid, preventing them from fraying or otherwise distorting as a thermal bonding of a soft-tip or a tubular stem member takes place.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts. These figures are provided to illustrate, and not limit, the present invention.

FIG. 1 is a perspective view of a diagnostic catheter constructed in accordance with the present invention;

FIG. 4 is a longitudinal cross-sectional view taken along the line 4—4 which passes through the joint between the tubular body stock and the stem member;

FIG. 5 is a longitudinal cross-sectional view taken through the distal end portion of the catheter along the line 5—5 in FIG. 1;

DESCRIPTION OF THE PREFERRED EMBODIMENTS

Figure 3:
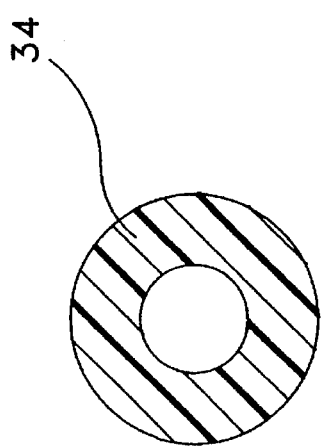
FIG. 3 is a cross-sectional view taken through the stem member of the catheter along the line 3—3 in FIG. 1.

Referring first to FIG. 1, there is indicated generally by numeral 10 a diagnostic catheter comprising the present invention. It includes an elongated tubular body 12 having a proximal end 14, a distal end 16 and a lumen 18 extending therebetween. Affixed to the proximal end 14 of the tubular body 12 is a molded plastic hub 20 having a Luer fitting 22 at its proximal end and flared wings 24 projecting radially from the diametrically opposed sides thereof to facilitate twisting of the catheter. An elastomeric sleeve 26 surrounds the proximal end portion of the tubular body 12 and functions as a strain relief member. The sleeve 26 is preferably roughened or knurled to facilitate gripping and rotation thereof using a three-finger catheter engagement. The length of the tubular body 12 will typically be 3 ½ to 4 feet in length and will have an outside diameter that is generally uniform over this length and will come in various sizes from, say, 3 Fr to 8 Fr.

Figure 2:
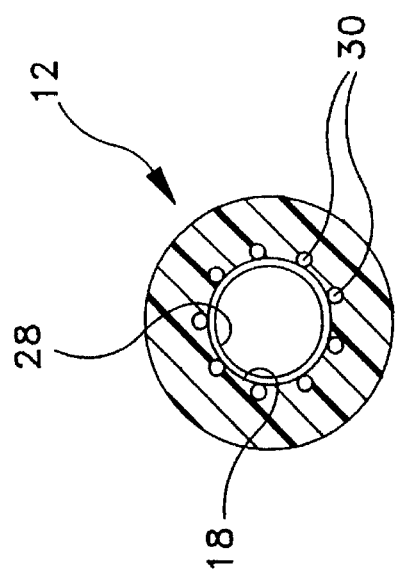
FIG. 2 is a cross-sectional view of the catheter of FIG. 1 taken along the line 2—2.

Referring to the cross-sectional view of FIG. 2, it can be seen that the tubular body 12 is formed with an inner layer 28 which is preferably a blend of about 10–25 weight percent 50D polyester-polyurethane and about 38–53 weight percent 70D polyester-polyurethane. With this material for the inner layer 28, the surface defining the lumen 18 is inherently lubricous. Moreover, polyester-polyurethane blends are found not to absorb moisture and, hence, will not change in dimension when immersed in saline, body fluids and/or contrast media liquid. The inner layer 12 preferably has a wall thickness in the range of from 0.001 to 0.008 inch (0.0025 to 0.0203 cm) with 0.0025±0.0005 inch (0.0064±0.0127 cm) being preferred.

As can also be seen in the cross-sectional views of FIGS. 2 and 4, a reinforcing means, in this case a braided sleeve of metal wires 30 is formed about the inner layer 28. More particularly, the inner layer 28 will typically be extruded over a polyacetal mandrel, and following extrusion, is braided using stainless steel braid wire. Any one of a number of braid patterns may be used including, without limitation, staggered 2-over-2-under or staggered 1-over-1-under. The braid angle may be adjusted to range anywhere from 20° to 60° from the perpendicular plane of the catheter. Again, without limitation, the braid wire diameter may fall in the range of from 0.0010 to 0.0030 inches (0.0025 to 0.0076 cm). As the wires are braided about the central inner layer 28, minor deformations occur at the point of contact between the braid wires and the inner layer, creating tiny irregularities in the surface of the lumen 18. It is found that these irregularities reduce the effective wall contact area between, say, a guidewire or an angioplasty catheter that might be inserted through the lumen, thereby reducing friction still further than is provided by the lubricous nature of the inner layer material itself.

Figure 6:
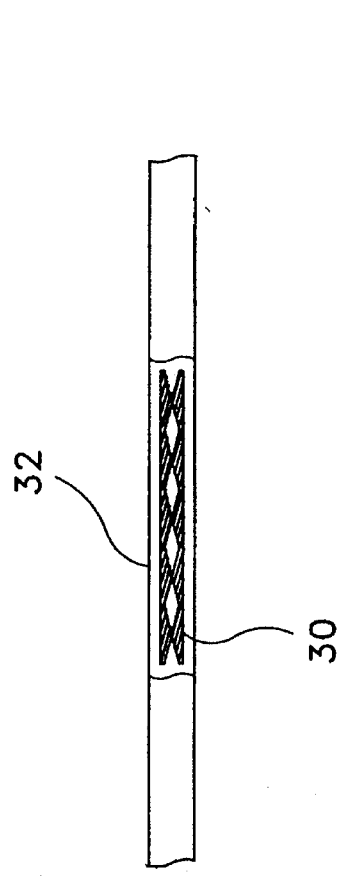
FIG. 6 is a cross-sectional view of a diagnostic catheter having a perforated metal tube as a reinforcing means.
Figure 7:
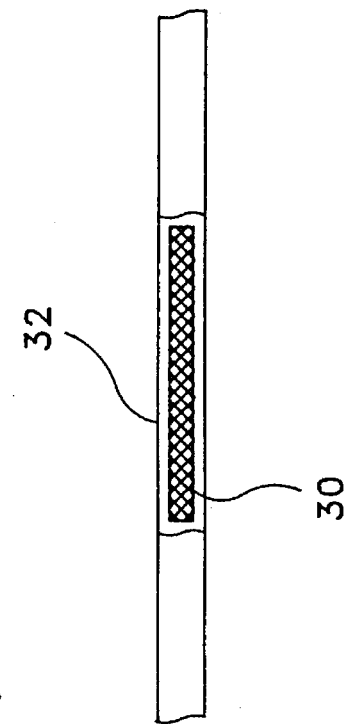
FIG. 7 is a cross-sectional view of a diagnostic catheter having a plastic mesh as a reinforcing means.

Alternative reinforcing means include a perforated metal tube, a perforated plastic tube, a plastic mesh, a contiguous plastic tube, and a plastic fabric. If a perforated tube is used, the tube may have perforations or slots of various shapes, such as ovals, circles, rectangles, or triangles with or without beveled edges. Methods of forming openings in metal tubes are disclosed in Kraus et al. (U.S. Pat. No. 5,256,144); and Samson et al. (U.S. Pat. No. 4,998,923). (All documents cited herein, including the foregoing, are incorporated herein by reference in their entireties for all purposes.) A plastic tube, plastic mesh and/or plastic fabric may comprise polymers such as polycarbonate, polyurethane, and polyethylene. FIG. 6 shows a catheter having a perforated metal tube as a reinforcing means 30, and FIG. 7 shows a plastic mesh as a reinforcing means 30.

Following placement of the reinforcing means, an outer layer 32 is extruded onto the assembly. The outer layer will preferably comprise a blend of about 10–25 weight percent 50D polyester-polyurethane and about 38–53 weight percent 70D polyester-polyurethane. The outer layer preferably contains a radiopaque filler, such as barium sulfate $BaSO_4$. As can be seen from the cross-sectional views of FIGS. 2 and 4, the outer layer 32 may totally embed the reinforcing means 30 and the die used with the extruder will provide a predetermined wall thickness yielding an outer diameter to the tubular body that is selected to be anywhere in the range of from 3 Fr to 8 Fr.

To provide a desired shape characteristic to the distal end portion of the diagnostic catheter, a tubular stem member 34 is thermally bonded to the distal end portion of the braided tubular body 12. As is best seen in FIG. 4, the braided tubular body has its outer layer or jacket 32 ground to a bevel as at 36. By beveling the distal end portion 16 of the tubular body 12, greater surface area is provided for effecting attachment of the stem member 34. In that the grinding operation used to create the bevel reduces the thickness of the outer jacket relative to the ends of the wires 30 comprising the braided sleeve, it has been found expedient to provide a band or ring 38 of a non-penetrable material surrounding the free ends of the braid wires. Without such a band, the heating required to effect a thermal bond between the tubular body 12 and the jacket 34 can cause the frayed ends of the braid to warp or bend to the point where they can penetrate through the inner layer 28 into the lumen 18 or through the thickness of the tubular stem 34. The band 38 confines those ends during heating, preventing such undesired wall penetration. With no limitation intended, the band of non-penetrable material may comprise a metal, such as tantalum, titanium, iridium, gold, silver, stainless steel and alloys of such materials. Alternatively, a suitable high temperature polymers, such as polyimide, e.g., KAPTON, can be used to constrain the free ends of the braid wires from penetrating the interior or exterior wall of the catheter during thermal bonding re-flow procedures.

The stem member 34 will preferably comprise a blend of about 10–25 weight percent 25D polyester-polyurethane and about 38–53 weight percent 70D polyester-polyurethane, along with a radiopaque filler, e.g., barium sulfate, being added, along with a desired pigment.

Preferred amounts of barium sulfate are 0–36 weight percent for the inner layer; 0–42 weight percent for the outer layer; and 0–42 weight percent for the stem. Additional materials may be included, such as pigments in the amounts of from 0.001–0.5 weight percent for the inner layer; 0.001–0.5 weight percent for the outer layer; and 0.001–0.5 weight percent for the stem. Additional materials that may be added include titanium dioxide, bismuth sub carbonate and iodine compounds.

Polyester-polyurethane materials are commercially available. Preferred materials are ESTANE® thermoplastic polyurethanes, made by B.F. Goodrich, and described in "Estane Thermoplastic Polyurethane, Product Data, USP XIX Class VI Estane Products" and in "Estane Thermoplastic Polyurethane, Product Data, Technical Service Report TSR 73-03/TF116, Extrusion of Estane Thermoplastic Polyurethanes." Examples of suitable polyester-polyurethane materials are described on the following table. Especially preferred are the following materials: for the inner layer—ESTANE® 58091/58277; for the outer layer—ESTANE® 58091/58277; and for the stem—ESTANE® 58091/58277.

| Property | * | Units | ASTM Method | 58091 | 58092 | 58134** | 58130** | 58277 | 58133** | 58137** | 58409 |
|---|---|---|---|---|---|---|---|---|---|---|---|
| Shore Hardness | B | A or D | D 2240 | 70 D | 45 D | 88 A/45 D | 82 A/50 D | 50 D | 55 D | 70 D | 48 D |
| Specific Gravity | B | — | D 792 | 1.15 | 1.22 | 1.20 | 1.21 | 1.21 | 1.22 | 1.23 | 1.22 |
| Tensile Strength | A | MPa | D 412 | 29 | 62 | 39 | 38 | 65 | 40 | 40 | 48 |
| Tensile Stress @ 100% Elongation | A | MPa | D 412 | (28) | 10 | 6.9 | 9.8 | 10 | 14 | 22 | 17 |
| Tensile Stress @ 300% Elongation | A | MPa | D 412 | — | 22 | 14 | 19 | 25 | 25 | 33 | 27 |
| Ultimate Elongation | A | % | D 412 | 160 | 480 | 590 | 550 | 480 | 510 | 440 | 470 |
| Tensile Set @ 200% Elongation | A | % | D 412$^{(1)}$ | — | 15 | — | — | 17 | — | — | — |
| Compression Set | | | | | | | | | | | |
| 22 hrs @ 23° C. | B | % | D 395 | 75 | 30 | 16 | 16 | 31 | 20 | 30 | 28 |
| 22 hrs @ 70° C. | B | % | D 395 | 98 | 80 | 65 | 80 | 79 | 70 | 80 | 64 |
| Stiffness | | | | | | | | | | | |
| @ 70° C. | C | MPa | D 747 | 352 | 25 | 22 | 32 | 23 | 43 | 58 | 24 |
| @ 23° C. | C | MPa | D 747 | 692 | 65 | 34 | 61 | 43 | 110 | 214 | 56 |
| @ −29° C. | C | MPa | D 747 | 2104 | 1280 | 135 | 409 | 1530 | 993 | 1690 | 1080 |
| Flex. Mod. @ 23° C. | C | MPa | D 790 | 1023 | 95 | 48 | 85 | 63 | 155 | 324 | 85 |
| Low Temperature Stiffness Modulars of Rigidity | | | | | | | | | | | |
| @ 23° C. | B | MPa | D 1053 | — | 13 | 10 | 15 | — | 20 | — | 13 |
| @ 0° C. | B | MPa | D 1053 | — | 32 | 17 | 25 | — | 39 | — | 32 |
| @ −20° C. | B | MPa | D 1053 | — | 133 | 32 | 69 | — | 138 | — | 132 |
| Vicot Softening Temperature (Method B) | B | °C. | D 1525 | 100 | 90 | 115 | 126 | 90 | 145 | 149 | 85 |
| Taber Abrasion: CS-16 Wheel 1,000 g load | B | mg/1,000 cycles | D 1044$^{(2)}$ | 200 | 3 | 3 | 3 | 3 | 7 | 12 | 2 |
| Tear Resistance | B | kN/m | D 624 | 193 | 119 | 107 | 133 | 107 | 158 | 228 | — |
| Split Tear | A | kN/m | D 470 | — | 27 | — | — | 28 | — | — | 27 |

*Sample Type (A) .025" (0.64 mm) extruded: (B) .075" (1.91 mm) milled and pressed; (C) .125" (3.18 mm., injection molded).
**Compounds 58134, 58130, 58133, 58137 used 126" (3.18 mm) injection molded samples for all testing.
$^{(1)}$Samples extended to 200% elongation, released immediately, allowed one minute to recover, then measured.
$^{(2)}$Samples tested for weight loss only, under specified wheel and load conditions.

Completing the catheter is a soft-tip member 40 which may be bonded to the distal end portion of the stem member 34. A suitable durometer for the soft-tip on the catheter, is 80A. That tip may be formed by injection molding the material onto the distal end of the stem member 34. Alternatively, if the catheter is not designed to include a stem member, the soft-tip 40 may be injection molded directly onto a distal end portion of the braided tubular body 12 with a impenetrable ring 38 again being used to confine the braiding wire ends as the soft tip is being formed.

Using the above techniques, it has been possible to produce a 3 Fr O.D. catheter having a lumen with a diameter of 0.026 inches (0.066 cm) and which still possesses excellent torquing characteristics whereby the distal end of the catheter follows a rotation of its proximal end. Moreover, even with such a relatively large diameter lumen in comparison to its outer diameter, the catheter still has adequate column strength allowing it to be advanced through the vascular system without kinking or buckling. An 8 Fr diagnostic catheter constructed in accordance with the present invention may have a lumen as large as 0.076 inches (0.193 cm), again having the desirable properties expected by most cardiologists as far as its ability to be manipulated through the application of longitudinal and rotational forces at the proximal end portion of the catheter.

Those skilled in the art will also appreciate that the intravascular catheter in accordance with the present invention can be manufactured to have a variety of different distal end shaped configurations to suit the desires of different cardiologists.

Various modifications and changes in detail may be made to the above-described embodiments and examples without departing from the spirit and scope of the invention. It is therefore intended that all such matter as described in the foregoing description and shown in the attached drawings be considered as illustrative only and not limiting.

What is claimed is:

1. An intravascular catheter comprising an elongated tubular body having a proximal portion, a distal portion and a lumen extending therebetween, said tubular body comprising:

(a) an inner layer comprising a blend of (i) about 10–25 weight percent of a polyester-polyurethane having a durometer of from about 45D–55D, and (ii) about 38–53 weight percent of a polyester polyurethane having a durometer of from about 65D–75D;

(b) a reinforcing means at least partially surrounding said inner layer; and (c) an outer layer comprising a blend of (i) about 10–25 weight percent of a polyester-polyurethane having a durometer of from about 4.D–55D, and (ii) about 38–53 weight percent of a polyester-polyurethane having a durometer of from about 65D–75D, said outer layer at least partially covering said reinforcing means.

2. The intravascular catheter of claim 1 and further including an annular soft-tip member bonded to said distal end of said tubular body member, said soft-tip member having a hardness of about 80A.

3. The intravascular catheter of claim 2 and further including a tubular stem member interposed between and bonded to both said tubular body and said soft-tip member, said stem member being a blend of (i) about 10–25 weight percent of a polyester-polyurethane having a durometer of from about 20D–30D, and (ii) about 38–53 weight percent of a polyester-polyurethane having a durometer of from about 65D–75D.

4. The intravascular catheter of claim 3 wherein the stem member comprises a blend of (i) about 10–25 weight percent 25D polyester-polyurethane and (ii) about 38–53 weight percent 70D polyester-polyurethane.

5. The intravascular catheter of claim 13 wherein said stem member includes a radiopaque filler material.

6. The intravascular catheter of claim 13 wherein said tubular body and said tubular stem have the same outer diameter.

7. The intravascular catheter of claim 13 wherein said tubular stem member is tapered from a first outside diameter equal to an outside diameter of said tubular body at a junction between said tubular body and said tubular stem member to a lesser diameter.

8. The intravascular catheter of claim 1, wherein (a) the inner layer comprises a blend of (i) about 10–25 weight percent 50D polyester-polyurethane, and (ii) about 38–53 weight percent 70D polyester polyurethane; and (c) the outer layer comprises a blend of (i) about 10–25 weight percent 50D polyester-polyurethane, and (ii) about 38–53 weight percent 70D polyester-polyurethane.

9. The intravascular catheter of claim 8 wherein said inner layer comprises a blend of (i) about 10 weight percent 50D polyester-polyurethane, and (ii) about 53 weight percent 70D polyester-polyurethane.

10. The intravascular catheter of claim 8 wherein said inner layer comprises a blend of (i) about 15 weight percent 50D polyester-polyurethane, and (ii) about 48 weight percent 70D polyester-polyurethane.

11. The intravascular catheter of claim 8 wherein said inner layer comprises a blend of (i) about 20 weight percent 50D polyester-polyurethane, and (ii) about 43 weight percent 70D polyester-polyurethane.

12. The intravascular catheter of claim 8 wherein said intravascular catheter has a wall thickness of about 0.0025 inches (0.0064 cm), and said wall thickness provides an outer diameter to said tubular body in the range of from 3 French to 8 French.

13. The intravascular catheter of claim 1 wherein said reinforcing means is totally embedded between said inner layer and said outer layer.

14. The intravascular catheter of claim 1 wherein said outer layer further comprises a radiopaque filler material.

15. The intravascular catheter of claim 1 wherein said lumen is of a diameter in the range of from about 0.026 to 0.080 inch (0.066 to 0.203 cm) and said outer layer has an outer diameter in the range of from about 0.039 to 0.110 inch (0.099 to 0.279 cm).

16. The intravascular catheter of claim 1 wherein said reinforcing means is a braided metal sleeve configuration of filaments and said sleeve extends from said proximal portion of the tubular body toward the distal portion of the tubular body by a predetermined distance.

17. The intravascular catheter of claim 1 wherein said reinforcing means is a perforated metal tube.

18. The intravascular catheter of claim 1 wherein said reinforcing means comprises a polymer forming a mesh, a tube, or a fabric.

19. An intravascular catheter comprising an elongated tubular body having a proximal portion, a distal portion and a lumen extending therebetween, said tubular body comprising:

(a) an inner layer comprising a blend of (i) about 10–25 weight percent of a polyester-polyurethane having a durometer of about 45D–55D, and (ii) about 38–53 weight percent of a polyester polyurethane having a durometer of about 65D–75D;

(b) a reinforcing means at least partially surrounding said inner layer;

(c) an outer layer comprising a blend of (i) about 10–25 weight percent of a polyester-polyurethane having a durometer of from about 45D–55D, and (ii) about 38–53 weight percent of a polyester-polyurethane having a durometer of from about 65D–75D, said outer layer at least partially covering said reinforcing means; and (d) a stem member comprising a blend of (i) about 10–25 weight percent of a polyester-polyurethane having a durometer of about 25D; and (ii) about 38–53 weight percent of a polyester-polyurethane having a durometer of about 70D.

20. An intravascular catheter comprising an elongated tubular body having a proximal portion, a distal portion and a lumen extending therebetween, said tubular body comprising:

(a) an inner layer comprising a blend of (i) about 10–25 weight percent of a polyester-polyurethane having a durometer of about 50D; and (ii) about 38–53 weight percent of a polyester polyurethane having a durometer of about 70D;

(b) a reinforcing means at least partially surrounding said inner layer;

(c) an outer layer comprising a blend of (i) about 10–25 weight percent of a polyester-polyurethane having a durometer of about 50D, and (ii) about 38–53 weight percent of a polyester-polyurethane having a durometer of about 70D, said outer layer at least partially covering said reinforcing means; and (d) a stem member comprising a blend of (i) about 10–25 weight percent 25D polyester-polyurethane, and (ii) about 38–53 weight percent 70D polyester-polyurethane.

21. An intravascular catheter comprising an elongated tubular body having a proximal portion, a distal portion and a lumen extending therebetween, said tubular body comprising:

(a) an inner layer comprising a "blend of (i) about 10–25 weight percent of a polyester-polyurethane having a durometer of about 45–55D, (ii) about 38–53 weight percent of a polyester polyurethane having a durometer of about 65D–75D, and (iii) about 0–36 weight percent barium sulfate;

(b) a reinforcing means at least partially surrounding said inner layer; and (c) an outer layer comprising a blend of (i) about 10–25 weight percent of a polyester-polyurethane having a durometer of from about 45–55D, (ii) about 38–53 weight percent of a polyester-polyurethane having a durometer of from about 65–75D, and (iii) about 0–42 weight percent barium sulfate, said outer layer at least partially covering said reinforcing means.

* * * * *